United States Patent
Rege et al.

(10) Patent No.: US 11,154,468 B2
(45) Date of Patent: *Oct. 26, 2021

(54) ORAL CARE COMPOSITIONS AND METHODS OF USE

(71) Applicant: Colgate-Palmolive Company, New York, NY (US)

(72) Inventors: Aarti Rege, East Windsor, NJ (US); Michael Prencipe, West Windsor, NJ (US); Paul Thomson, Piscatatway, NJ (US)

(73) Assignee: Colgate-Palmolive Company, New York, NY (US)

( * ) Notice: Subject to any disclaimer, the term of this patent is extended or adjusted under 35 U.S.C. 154(b) by 322 days.

This patent is subject to a terminal disclaimer.

(21) Appl. No.: 15/708,556

(22) Filed: Sep. 19, 2017

(65) Prior Publication Data

US 2018/0168956 A1    Jun. 21, 2018

Related U.S. Application Data

(60) Provisional application No. 62/437,095, filed on Dec. 21, 2016.

(51) Int. Cl.

| | |
|---|---|
| *A61K 8/24* | (2006.01) |
| *A61K 8/27* | (2006.01) |
| *A61Q 11/00* | (2006.01) |
| *A61K 8/19* | (2006.01) |
| *A61K 8/21* | (2006.01) |
| *A61K 8/34* | (2006.01) |
| *A61K 8/81* | (2006.01) |
| *A61K 8/362* | (2006.01) |
| *A61K 8/365* | (2006.01) |

(52) U.S. Cl.
CPC ............ *A61K 8/24* (2013.01); *A61K 8/19* (2013.01); *A61K 8/21* (2013.01); *A61K 8/27* (2013.01); *A61K 8/345* (2013.01); *A61K 8/362* (2013.01); *A61K 8/8164* (2013.01); *A61Q 11/00* (2013.01); *A61K 8/365* (2013.01)

(58) Field of Classification Search
CPC ... A61K 8/24; A61K 8/19; A61K 8/21; A61K 8/27; A61K 8/345; A61K 8/362; A61K 8/8164; A61K 8/365

USPC ........................................................ 424/52
See application file for complete search history.

(56) References Cited

U.S. PATENT DOCUMENTS

| | | | |
|---|---|---|---|
| 2,876,166 A | 3/1959 | Nebergall | |
| 4,961,924 A | 10/1990 | Suhonen | |
| 5,188,820 A | 2/1993 | Cummins et al. | |
| 5,578,293 A | 11/1996 | Prencipe et al. | |
| 5,833,952 A * | 11/1998 | Grigor | A61K 8/24 424/49 |
| 6,685,920 B2 | 2/2004 | Baig et al. | |
| 6,696,045 B2 | 2/2004 | Yue et al. | |
| 8,906,347 B2 | 12/2014 | Strand et al. | |
| 9,486,396 B2 | 11/2016 | Maloney et al. | |
| 2010/0278991 A1 * | 11/2010 | Haught | A61K 8/19 426/532 |
| 2012/0207686 A1 | 8/2012 | Fruge et al. | |
| 2013/0209375 A1 | 8/2013 | Moya Argilagos et al. | |
| 2014/0086851 A1 * | 3/2014 | Fisher | A61K 8/19 424/57 |
| 2015/0297500 A1 | 10/2015 | Robinson et al. | |
| 2015/0328094 A1 | 11/2015 | Xu et al. | |
| 2015/0335541 A1 | 11/2015 | Xu et al. | |
| 2016/0303010 A1 | 10/2016 | Prencipe et al. | |
| 2017/0128329 A1 | 5/2017 | Vemishetti et al. | |
| 2017/0319447 A1 | 11/2017 | Vemishetti et al. | |
| 2017/0367939 A1 | 12/2017 | Thomson et al. | |
| 2017/0367948 A1 | 12/2017 | Thomson et al. | |
| 2018/0028423 A1 | 2/2018 | Thomson et al. | |

FOREIGN PATENT DOCUMENTS

WO    WO 2014088573    *    6/2014    ............... A61K 8/27

OTHER PUBLICATIONS

International Search Report and Written Opinion of the International Searching Authority in International Application No. PCT/US2017/052183, dated Nov. 22, 2017.

Larba et al., 2013, "Citric acid as an alternative lixiviant for zinc oxide dissolution," Hydrometallurgy 134-135:117-123.

* cited by examiner

*Primary Examiner* — Adam C Milligan

(57) ABSTRACT

This invention relates to oral care compositions comprising a zinc source comprising zinc oxide and zinc citrate; a stannous source comprising stannous pyrophosphate; a fluoride ion source comprising sodium fluoride; and an organic buffer, as well as to methods of using and of making these compositions.

9 Claims, No Drawings

ORAL CARE COMPOSITIONS AND METHODS OF USE

CROSS-REFERENCE TO RELATED PATENT APPLICATION

This application claims priority from U.S. Prov. Appl. No. 62/137,095, filed on Dec. 21, 2016, the contents of which are incorporated herein by reference in their entirety,

FIELD OF THE DISCLOSURE

This invention relates to oral care compositions comprising a zinc source comprising zinc oxide and zinc citrate; a stannous source comprising stannous pyrophosphate; a fluoride ion source comprising sodium fluoride; and an organic buffer system, as well as to methods of using and of making these compositions.

BACKGROUND

Zinc is a known antimicrobial agent used in toothpaste compositions. Zinc is a known essential mineral for human health, and has been reported to help strengthen dental enamel and to promote cell repair.

Stannous ions, in particular stannous salts such as stannous fluoride, are also known anti-microbial agents and are used in various dentifrices as agents for preventing plaque. However, there are certain disadvantages to using stannous salts, such as instability, tendency to stain teeth, astringency, and unpleasant taste for users.

Accordingly, in view of the drawbacks and disadvantages to using various antimicrobials, such as zinc and stannous, there is a need for oral care compositions with anti-bacterial efficacy, but which are also palatable and desirable for a user.

BRIEF SUMMARY

It has been surprisingly found that the current formulations offer the advantage of robust microbial protection without significantly interfering with the stability of the oral care composition. It is an unexpected benefit that that current formulation use comparable amounts of stannous and zinc than previous formulations, but still maintain or improve the availability of stannous in the oral cavity of a user.

In one aspect the invention is an oral care composition (Composition 1.0) comprising:
a. A zinc source comprising zinc oxide and zinc citrate;
b. A stannous source comprising stannous pyrophosphate;
c. A fluoride ion source (e.g., sodium fluoride); and
d. An organic acid buffer (e.g., An aqueous buffer comprising citric acid and tri-sodium citrate).

For example, the invention contemplates any of the following compositions (unless otherwise indicated, values are given as percentage of the overall weight of the composition)

1.1 Composition 1.0, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.2 Any of the preceding compositions comprising zinc citrate and zinc oxide, wherein the zinc citrate is in an amount of from 0.25 to 1 wt % (e.g., 0.5 wt. %) and zinc oxide may be present in an amount of from 0.75 to 1.25 wt % (e.g., 1.0 wt. %) based on the weight of the oral care composition.

1.3 Any of the preceding compositions wherein the zinc citrate is about 0.5 wt %.

1.4 Any of the preceding compositions wherein the zinc oxide is about 1.0 wt %.

1.5 Any of the preceding compositions where the zinc citrate is about 0.5 wt % and the zinc oxide is about 1.0 wt %.

1.6 Any of the preceding compositions, wherein the zinc oxide is about 1.0 wt %.

1.7 Any of the preceding compositions, where the zinc citrate is about 0.8 wt % (e.g., about 0.85 wt. %) and the zinc oxide is about 1.0 wt %.

1.8 Any of the preceding compositions, wherein the stannous ion source further comprises stannous fluoride, other stannous halides such as stannous chloride dihydrate, organic stannous carboxylate salts such as stannous formate, acetate, gluconate, lactate, tartrate, oxalate, malonate and citrate, stannous ethylene glyoxide, or a mixture thereof.

1.9 Any of the preceding compositions, wherein the stannous pyrophosphate is present in an amount of 0.1 wt. % to 2 wt. % (e.g., about 1.0 wt. %) of the total composition weight.

1.10 Any of the preceding compositions, wherein the composition comprises a copolymer.

1.11 The composition of 1.10, wherein the copolymer is a PVM/MA copolymer.

1.12 The composition of 1.11, wherein the PVM/MA copolymer comprises a 1:4 to 4:1 copolymer of maleic anhydride or acid with a further polymerizable ethylenically unsaturated monomer; for example 1:4 to 4:1, e.g. about 1:1.

1.13 Any of the preceding compositions, wherein the further polymerizable ethylenically unsaturated monomer comprises methyl vinyl ether (methoxyethylene).

1.14 Any of the preceding compositions, wherein the PVM/MA copolymer comprises a copolymer of methyl vinyl ether/maleic anhydride, wherein the anhydride is hydrolyzed following copolymerization to provide the corresponding acid.

1.15 Any of the preceding compositions, wherein the PVM/MA copolymer comprises a GANTREZ® polymer (e.g., GANTREZ® S-97 polymer)

1.16 Any of the preceding compositions wherein the pH is between 7.5 and 10.5. e.g., about 7.5 or about 8.0.

1.17 Any of the preceding compositions, wherein the sodium fluoride is present in an amount from 0.1%-1.0% by wt. (e.g., about 0.24% by wt.).

1.18 Any of the preceding compositions, wherein the fluoride ion source further comprises one of the following ingredients selected from the group consisting of stannous fluoride, potassium fluoride, sodium monofluorophosphate, sodium fluorosilicate, ammonium fluorosilicate, amine fluoride, ammonium fluoride, and combinations thereof.

1.19 Any of the preceding compositions further comprising a polyphosphate 1.20 A composition of 1.19, wherein the polyphosphate is sodium tripolyphosphate (STPP).

1.21 The composition of 1.20, wherein the sodium tripolyphosphate is from 0.5-5.0 wt % (e.g., about 3.0 wt %).

1.22 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, disodium hydrogenorthophoshpate, monosodium phosphate, pentapotassium triphosphate and mixtures of any of two or more of these, e.g., in an amount of 1-20%, e.g., 2-8%, e.g., ca. 5%>, by weight of the composition.

1.23 Composition of 1.22, wherein the alkali phosphate salt is tetrasodium pyrophosphate.

1.24 Any of the preceding compositions further comprising an abrasive or particulate (e.g., silica).

1.25 The composition of 1.30, wherein the abrasive or particulate is selected from sodium bicarbonate, calcium phosphate (e.g., dicalcium phosphate dihydrate), calcium sulfate, precipitated calcium carbonate, calcium pyrophosphate, silica (e.g., hydrated silica), iron oxide, aluminum oxide, perlite, plastic particles, e.g., polyethylene, and combinations thereof.

1.26 Any of the preceding compositions wherein the silica is synthetic amorphous silica. (e.g., 1%-25% by wt.) (e.g., about 5.5% by wt.)

1.27 Any of the preceding composition wherein the silica abrasives are silica gels or precipitated amorphous silicas, e.g. silicas having an average particle size ranging from 2.5 microns to 12 microns.

1.28 Any of the preceding compositions further comprising a small particle silica having a median particle size (d50) of 1-5 microns (e.g., 3-4 microns) (e.g., about 5 wt. % Sorbosil AC43 from Ineos Silicas, Warrington, United Kingdom).

1.29 Any of the preceding compositions wherein 20-30 wt % of the total silica in the composition is small particle silica (e.g., having a median particle size (d50) of 3-4 microns) and wherein the small particle silica is about 5 wt. % of the oral care composition.

1.30 Any of the preceding compositions comprising silica wherein the silica is used as a thickening agent, e.g., particle silica.

1.31 Any of the preceding compositions further comprising an anionic surfactant, wherein the nonionic surfactant is in an amount of from 0.5-5% by wt., e.g., 1-2% by weight (e.g., about 1.75% by wt.), selected from water-soluble salts of higher fatty acid monoglyceride monosulfates, (e.g., sodium N-methyl N-cocoyl taurate), sodium cocomo-glyceride sulfate; higher alkyl sulfates, (e.g., sodium lauryl sulfate); higher alkyl-ether sulfates (e.g., of formula $CH_3(CH_2)_mCH_2(OCH_2CH_2)_nOSO_3X$, wherein m is 6-16, e.g., 10, n is 1-6, e.g., 2, 3 or 4, and X is Na) or (e.g., sodium laureth-2 sulfate $(CH_3(CH_2)_{10}CH_2(OCH_2CH_2)_2OSO_3Na)$; higher alkyl aryl sulfonates (e.g., sodium dodecyl benzene sulfonate, sodium lauryl benzene sulfonate); higher alkyl sulfoacetates (e.g., sodium lauryl sulfoacetate; dodecyl sodium sulfoacetate), higher fatty acid esters of 1,2 dihydroxy propane sulfonate, sulfocolaurate (e.g., N-2-ethyl laurate potassium sulfoacetamide) and sodium lauryl sarcosinate, and mixtures thereof.

1.32 Any of the preceding compositions, wherein the anionic surfactant is sodium lauryl sulfate (e.g., about 1.75 by wt.).

1.33 Any of the preceding compositions further comprising glycerin, wherein the glycerin is in a total amount of 20-50% (e.g., about 41% by wt.).

1.34 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.35 Any of the preceding compositions, wherein the zinc citrate is in an amount of from 0.25 to 1 wt % (e.g., 0.5 wt. %) and zinc oxide may be present in an amount of from 0.75 to 1.25 wt % (e.g., 1.0 wt. %) based on the weight of the oral care composition.

1.36 Any of the preceding compositions wherein the zinc citrate is about 0.5 wt %.

1.37 Any of the preceding compositions wherein the zinc oxide is about 1.0 wt %.

1.38 Any of the preceding compositions where the zinc citrate is about 0.5 wt % and the zinc oxide is about 1.0 wt %.

1.39 Any of the preceding compositions comprising polymer films.

1.40 Any of the preceding compositions comprising flavoring, fragrance and/or coloring.

1.41 The composition of 1.46, wherein the flavoring agent is sodium saccharin, sucralose, or a mixture thereof.

1.42 Any of the preceding compositions, wherein the composition comprises a thickening agents selected from the group consisting of carboxyvinyl polymers, carrageenan, xanthan, hydroxyethyl cellulose and water soluble salts of cellulose ethers (e.g., sodium carboxymethyl cellulose and sodium carboxymethyl hydroxyethyl cellulose).

1.43 Any of the preceding compositions, wherein the compositions comprises sodium carboxymethyl cellulose (e.g., from 0.1 wt. %-2.5 wt. %) (e.g., about 0.2% by wt.).

1.44 Any of the preceding compositions comprising from 5%-40%, e.g., 10%-35%, e.g., about 10, about 12%, about 15%, about 25%, about 30%/o, and about 35% water.

1.45 Any of the preceding compositions comprising an additional antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.46 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

1.47 Any of the preceding compositions comprising a whitening agent.

1.48 The composition of 1.40, wherein the whitening agent is titanium dioxide.

1.49 Any of the preceding compositions comprising a whitening agent selected from a whitening active selected from the group consisting of peroxides, metal chlorites, perborates, percarbonates, peroxyacids, hypochlorites, and combinations thereof.

1.50 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.51 Any of the preceding compositions further comprising an agent that interferes with or prevents bacterial attachment, e.g., ELA or chitosan.

1.52 Any of the preceding compositions, wherein the organic acid buffer comprises an acid select from: citric acid, formic acid, fumaric acid, lactic acid, gluconic acid, oxalic acid, succinic acid, phytic acid and combinations thereof.

1.53 Any of the preceding compositions, wherein the organic acid buffer is a citrate buffer, wherein the citrate buffer is an aqueous buffer comprising an organic acid and an alkali metal salt thereof, e.g., where the composition comprises 1-10%, by weight organic acid salt and 0.1-5% by weight organic acid (e.g., where the buffer is in an amount about 2.1% by wt.)

1.54 Any of the preceding compositions, wherein the citrate buffer comprises about 1.5% by wt. tri-sodium citrate and about 0.6% by wt. citric acid.

1.55 Any of the preceding compositions, wherein the amount of stannous pyrophosphate is from 0.10%-3% by wt. of the composition. (e.g., about 1% by wt. of the composition).

1.56 Any of the preceeding compositions wherein the amount of stannous pyrophosphate is about 0.2% by wt.

1.57 Any of the preceding compositions wherein the amount of stannous pyrophosphate is about 0.3% by wt.

1.58 Any of the preceding compositions wherein the amount of stannous pyrophosphate is about 0.5% by wt.

1.59 Any of the preceding compositions wherein the amount of stannous pyrophosphate is about 0.75% by wt.

1.60 Any of the preceding compositions wherein the amount of stannous pyrophosphate is about 1.0% by wt.

1.61 Any of the preceding compositions comprising:
  a. about 1.0% zinc oxide
  b. about 0.5% zinc citrate
  c. about 0.24% sodium fluoride;
  d. about 1.5% of sodium citrate (e.g., trisodium citrate dehydrate);
  e. about 0.6% citric acid (e.g., citric acid—anhydrous USP).

1.62 Any of the preceding compositions comprising:
  a. about 1.0% zinc oxide
  b. about 0.5% zinc citrate
  c. about 0.24% sodium fluoride;
  d. about 1.5% of sodium citrate (e.g., trisodium citrate dehydrate);
  e. about 0.6% citric acid (e.g., citric acid—anhydrous USP).
  f. about 1.0% stannous pyrophosphate
  g. about 2.0% tetrasodium pyrophosphate 1.63 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit malodor, (vi) promote healing of sores or cuts in the mouth, (vii) reduce levels of acid producing bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.64 Any of the preceding oral compositions, wherein the oral composition may be any of the following oral compositions selected from the group consisting of: a toothpaste or a dentifrice, a mouthwash or a mouth rinse, a topical oral gel, a denture cleanser, a coated or impregnated immediate or delayed release oral adhesive strip or patch, and a coated or impregnated oral wipe or swab.

1.65 Any of the preceding compositions, where the only sources of zinc are zinc oxide and zinc citrate and zinc phosphate.

1.66 Any of the preceding compositions, where the only source of stannous is stannous pyrophosphate.

1.67 A composition obtained or obtainable by combining the ingredients as set forth in any of the preceding compositions.

A composition for use as set for in any of the preceding compositions.

In another embodiment, the invention encompasses a method to improve oral health comprising applying an effective amount of the oral composition of any of the embodiments (e.g., any of Compositions 1.0 et seq) set forth above to the oral cavity of a subject in need thereof, e.g., a method to
  i. reduce or inhibit formation of dental caries,
  ii. reduce levels of acid producing bacteria,
  iii. inhibit microbial bio film formation in the oral cavity,
  iv. reduce plaque accumulation,
  v. immunize (or protect) the teeth against cariogenic bacteria and their effects, and/or
  vi. clean the teeth and oral cavity.

The invention further comprises the use of sodium bicarbonate, sodium methyl cocoyl taurate (tauranol), MIT, and benzyl alcohol and combinations thereof in the manufacture of a Composition of the Invention, e.g., for use in any of the indications set forth in the above method of Composition 1.0, et seq.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively the oral composition may be dual phase dispensed from a separated compartment dispenser.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, e.g., the Compositions of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., about 1.75% by wt.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of Composition 1.0, et seq., that can be used in the compositions of the invention include betaines (e.g., cocamidopropyl), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1%0/by weight.

pH Adjusting Agents

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates (e.g., monopotassium phosphate, monosodium phosphate, disodium phosphate, dipotassium phosphate, tribasic sodium phosphate, sodium tripolyphosphate, pentapotassium tripolyphosphate, phosphoric acid), citrates (e.g. citric acid, trisodium citrate dehydrate), pyrophosphates (sodium and potassium salts, e.g., tetrapotassium pyrophosphate) and combinations thereof. The amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%, in another embodiment about 15% to about 25%, by weight of the total composition.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.1 wt. % pyrophosphate ions, e.g., 0.1 to 3 wt. %, e.g., 0.1 to 2 wt. %, e.g., 0.1 to 1 wt. %, e.g., 0.2 to 0.5 wt %. The pyrophosphates also contribute to preservation of the compositions by lowering water activity.

Suitable anticalculus agents for the invention (e.g., Composition 1.0 et seq) include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In particular embodiments, the invention includes alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP) ($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Polymers

The oral care compositions of the invention also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, polyvinyl pyrrolidone, carrageenan, xanthan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_1(PO_4)_6(OH)_2$), or dicalcium phosphate dihydrate ($CaHPO_4.2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example synthetic amorphous silica. Silica may also be available as a thickening agent, e.g., particle silica. For example, the silica can also be small particle silica (e.g., Sorbosil AC43 from PQ Corporation, Warrington, United Kingdom). However the additional abrasives are preferably not present in a type or amount so as to increase the RDA of the dentifrice to levels which could damage sensitive teeth, e.g., greater than 130.

Water

Water is present in the oral compositions of the invention. Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

Within certain embodiments of the oral compositions, it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerin, sorbitol, xylitol, propylene glycol as well as other polyols and mixtures of these humectants. Mixtures of glycerin and sorbitol may be used in certain embodiments as the humectant component of the compositions herein.

The present invention in its method aspect involves applying to the oral cavity a safe and effective amount of the compositions described herein.

The compositions and methods according to the invention (e.g., Composition 1.0 et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Test Formulations of the present invention comprising 0.24% NaF, 1.0% ZnO and 0.5% Zn Citrate, 1% Stannous Pyrophoshpate and 2.1% Citrate Buffer System are tested against market formulations with Zn Lactate and SnF. The formulations are tested using an in vitro method to determine the metal ion uptake on the surface of 10 mm bovine blocks after pellicle growth, 1% citric acid challenge, and treatment of the test dentifrice and dissolution of the surface using 6% citric acid.

The control groups (positive and negative controls), and tested groups, each contain bovine blocks, and bovine block is about 10 mm in diameter. Control and test formulations are applied to the bovine blocks. Some blocks are subject to negative control formulations (Water/untreated). The method includes treatment with saliva for 2-12 hrs acid etch, rinse, and treatment 2 mins. Other blocks (Test blocks) are subject to positive control formulations (Market Formulation containing Zn Lactate and SnF) and test formulations (Formulations comprising 0.24% NaF, 1.0% ZnO and 0.5% Zn Citrate, 1% Stannous Pyrophoshpate and 2.1% Citrate Buffer System) Test blocks are subject to saliva for 2 hr, acid etch, rinse, treatment 2 mins, rinse. All bovine blocks are subject to 6% citric acid treatment for 1 hr. Acid is removed and analyzed. Values below are normalized to the negative control formulations (e.g., Baseline="1").

Test formulations comprise about 0.24% NaF with 1% Stannous Pyrophosphate, 1.0% Zinc Oxide, 0.5% Zinc Citrate, 2% Tetrasodium pyrophoshpate and 2.1% citrate buffer system (an aqueous buffer comprising 0.6% citric acid and 1.5% tri-sodium citrate). There is improved zinc uptake in bovine block tests when compared to formulations which contain $SnF_2$ and zinc lactate (but not ZnO and Zn Citrate)):

TABLE 1

|  | Total Stannous uptake* (ppm) | Total Zinc uptake* (ppm) |
| --- | --- | --- |
| Control Formulation ($SnF_2$ and zinc lactate) | 0.81 | 1.74 |
| Test Formulation | 0.64 | 2.63 |

*Values normalized to untreated negative control Baseline = "1")

Example 2

Test Formula referenced in Example 1 above (values are % wt. of composition).

TABLE 2

| Description | Weight % |
| --- | --- |
| Humectant | 35%-50% |
| Abrasive | 15.0%-25% |
| pH Adjusting Agent | 0.1%-1.0% |
| Polymer | 0.1%-4% |
| Colorant, Flavoring Agent | 1.0%-2.0% |
| Amphoteric Surfactant | 0.5%-2.0% |
| Thickening agent | 0.5%-3.5% |

TABLE 2-continued

| Description | Weight % |
| --- | --- |
| Sodium Fluoride, USP | 0.24% |
| Demineralized Water | Q.S. (e.g., 10%-20%) |
| Anionic Surfactant | 1.0%-2.5% |
| Zinc Oxide | 1% |
| Alkali Phosphate Salt | 0%-3.0% |
| Zinc Citrate (e.g., Zinc Citrate Trihydrate) | 0.5% |
| Stannous Pyrophosphate | 1.0% |
| Trisodium Citrate Dihydrate - USP | 1.5% |
| Citric Acid - Anhydrous USP | 0.6% |
| Total Components | 100% |

The invention claimed is:

1. An oral care composition comprising:
   a. A zinc source comprising zinc citrate and zinc oxide, wherein the zinc citrate is in an amount of 0.5 wt % and zinc oxide is present in an amount of 1 wt % based on the total weight of the composition;
   b. A stannous source comprising stannous pyrophosphate, wherein the stannous pyrophosphate is present in an amount of 1 wt % based on the total weight of the composition;
   c. A fluoride ion source comprising 0.24% by wt sodium fluoride; and
   d. An organic acid buffer, wherein the organic acid buffer is a citrate buffer, wherein the citrate buffer is in an amount of 2.1% by wt and comprises citric acid and tri-sodium citrate; and
wherein the oral composition is selected from the group consisting of: a toothpaste, a mouthwash, a topical oral gel, and a denture cleanser.

2. The oral care composition of claim 1, wherein the citric acid is in an amount about 0.6% by wt., and the tri-sodium citrate is in an amount about 1.5% by wt.

3. The oral care composition of claim 1, wherein composition comprises a copolymer.

4. The oral care composition of claim 3, wherein the copolymer is a PVM/MA copolymer.

5. The oral care composition of claim 1, wherein the composition further comprises sodium tripolyphosphate.

6. The oral care composition of claim 5, wherein the sodium tripolyphosphate is present in an amount of from 0.5-5.0 wt %, based on the total weight of the composition.

7. The oral care composition of claim 1, wherein the composition further comprises glycerin, wherein the glycerin is in a total amount of 20-50%, based on the total weight of the composition.

8. The oral care composition of claim 1 comprising a whitening agent.

9. A method to improve oral health comprising applying an effective amount of the oral composition of claim 1 to the oral cavity of a subject in need thereof.

* * * * *